United States Patent
Vega (10) Patent No.: US 7,349,812 B2
(45) Date of Patent: Mar. 25, 2008

(54) METHOD FOR DETERMINING THE TITER OF BIOLOGICAL AGENTS IN LIVING TARGET CELLS

(75) Inventor: Manuel Vega, Vigneux-sur-Seine (FR)

(73) Assignee: Nautilus Biotech, Evry (FR)

( * ) Notice: Subject to any disclaimer, the term of this patent is extended or adjusted under 35 U.S.C. 154(b) by 0 days.

(21) Appl. No.: 11/412,939

(22) Filed: Apr. 28, 2006

(65) Prior Publication Data

US 2006/0195268 A1    Aug. 31, 2006

Related U.S. Application Data

(62) Division of application No. 10/275,253, filed as application No. PCT/FR01/01366 on May 4, 2001, now abandoned.

(30) Foreign Application Priority Data

May 9, 2000   (FR)   ................... 00 05852

(51) Int. Cl.
G06F 17/11   (2006.01)
G06F 17/50   (2006.01)
G06F 19/00   (2006.01)

(52) U.S. Cl. ......................... 702/19; 702/23
(58) Field of Classification Search .................. 702/19, 702/23
See application file for complete search history.

(56) References Cited

U.S. PATENT DOCUMENTS

| 5,691,155 A | 11/1997 | Nahmias et al. |
| 6,444,428 B1 | 9/2002 | Hogrefe |
| 2003/0129203 A1 | 7/2003 | Vega et al. |
| 2003/0129584 A1 | 7/2003 | Vega |
| 2003/0134351 A1 | 7/2003 | Vega et al. |
| 2003/0224404 A1 | 12/2003 | Vega et al. |
| 2004/0132977 A1 | 7/2004 | Gantier et al. |
| 2005/0202438 A1 | 9/2005 | Gantier et al. |
| 2006/0020116 A1 | 1/2006 | Gantier et al. |
| 2006/0020396 A1 | 1/2006 | Gantier et al. |
| 2006/0094655 A1 | 5/2006 | Guyon et al. |

FOREIGN PATENT DOCUMENTS

WO   99 11764   3/1999

OTHER PUBLICATIONS

Tavoloni N. PubMed ID: 9081705. Gene Therapy, (Feb. 1997) vol. 4, No. 2, pp. 150-155.*
P. Charbord et al.: "Normal human granulo monocytic bone marrow progenitor cells responsiveness to colony stimulating activity" Nouvelle Revue Francaise D'Hematologie, vol. 22, pp. 357-370 1980.
Klaus Schuhmann et al.: "Intracelluar Ca2+ Inhibits smooth muscle L-type Ca2+ channels by activation of protein phosphatase type 2B and by direct Interaction with the channel" Journal of General Physiology, vol. 110, pp. 503-513 Nov. 1997.
P. Moullier et al.: "Comparative binding of wheat germ agglutinin and its succinylated form on lymphocytes" European Journal of Biochemistry; vol. 161, pp. 197-204 1986.
A.R. Davis et al.: "High throughput method for creating and screening recombinant adenoviruses" Gene Therapy, vol. 5, No. 8, pp. 1148-1152 Aug. 1998.
E.M. Atkinson et al.: "A high-throughput hybridization method for titer determination of viruses and gene therapy vectors" Nucleic Acids Research, vol. 26, No. 11, pp. 2821-2823 Jun. 1, 1998.
David M. Nelson et al.: "Characterization of diverse viral vector preparations, using a simple and rapid whole-virlon dot-blot method" Human Gene Therapy, vol. 9, pp. 2401-2405 Nov. 1, 1998.
Nanette Mittereder et al.: "Evaluation of the concentration and bioactivity of adenovirus vectors for gene therapy" Journal of Virology, vol. 70, No. 11, pp. 7498-7509 Nov. 1996.
A. Salvetti et al.: "Factors Influencing recombinant adeno-associated virus production" Human Gene Therapy, vol. 9, No. 5, pp. 695-706 Mar. 20, 1998.
Stratagene Corp. QuikChange® site-directed mutagenesis kit. Product Information, date not available.

* cited by examiner

*Primary Examiner*—Michael Borin
(74) *Attorney, Agent, or Firm*—Oblon, Spivak, McClelland, Maier & Neustadt, P.C.

(57) ABSTRACT

Method for determining the titer (concentration) of biological agents, such as viral vectors for gene transfer, in real time, in living target cells and uses thereof in the field of gene therapy and diagnosis.

7 Claims, 8 Drawing Sheets

Figure 1

| conc. | temps (h) | | | | |
|---|---|---|---|---|---|
| | 16 | 24 | 40 | 48 | 64 |
| 0.1 | 20.4 | 30.1 | 95.1 | 138.7 | 157.3 |
| 0.25 | 26.8 | 48.5 | 173.3 | 228.2 | 191.7 |
| 0.5 | 38.1 | 72 | 198.7 | 296.2 | 203.7 |

Figure 3

| conc. | 0.1 | 0.25 | 0.5 |
|---|---|---|---|
| $t_\beta$ (h) | 42 | 31 | 28 |

| conc. | time (h) | | | | | | | | | |
|---|---|---|---|---|---|---|---|---|---|---|
| | 6 | 14 | 18 | 20 | 24 | 30 | 38 | 44 | 48 | 54 |
| 10exp-4 | 1.62 | 1.81 | 2.41 | 2.61 | 2.85 | 3.38 | 3.61 | 4.01 | 3.89 | 3.67 |
| 10exp-7 | 1.37 | 1.33 | 1.61 | 1.73 | 2.05 | 2.67 | 2.96 | 3.23 | 3.29 | 3.17 |
| 10exp-8 | 1.29 | 1.32 | 1.41 | 1.36 | 1.59 | 1.96 | 2.32 | 2.58 | 2.81 | 2.46 |
| 10exp-9 | 1.31 | 1.32 | 1.41 | 1.38 | 1.48 | 1.65 | 2.02 | 2.22 | 2.45 | 2.19 |

| Conc (log) | $t_g$ (h) |
|---|---|
| .4 | 15 |
| .7 | 23.5 |
| .8 | 30 |
| .9 | 39 |

Figure 8

METHOD FOR DETERMINING THE TITER OF BIOLOGICAL AGENTS IN LIVING TARGET CELLS

The invention concerns a method for determining the titer (concentration) of biological agents, such as gene transfer viral vectors, in real time, in living target cells, as well as its uses (gene therapy, functional genomics, viral diagnosis, vaccines, recombinant proteins).

The progress concerning gene transfer in the field of gene therapy depends, on the one hand on the capacity to develop and to produce vectors allowing, a regulated expression in the target cell, of a protein or an RNA which possess therapeutic effects, and on the other hand on the capacity to identify new therapeutic genes.

Thus, with the recent development in the field of functional genomics, vectors initially developed for gene transfer, are also used as tools for the screening of gene libraries.

These progresses imply:
the construction and the screening of gene transfer vectors libraries,
the development of optimized vector constructs which are perfectly adapted to each therapeutic application, in particular in terms of tissue-targeting and expression regulation, and
the production in large quantities of controlled, standardized vectors with an optimal quality, which can be used in preclinical studies and phase I clinical trials.

In this context, in order to analyze quickly numerous vector constructs and to optimize their production in large quantities, it is important to be able to determine easily, quickly and accurately the concentration of said vectors by efficient methods.

The methods for determining the concentration or the titer of said vectors, in particular of the viral vectors, described in the literature are divided into physical methods and biological methods.

The physical methods measure the titer of physical particles (pp) (Mittereder et al., J. Virol., 1996, 70, 11, 7498-7509; Atkinson et al., NAR, 1998, 26, 11, 2821-2823; Nelson et al., Hum. Gene Ther., 1998, 9, 16, 2401-2405), which represents the total number of viral vector particles; usually this titer is estimated either directly by counting the viral particles by electronic microscopy, or indirectly by measuring the nucleic acid content of the vectors (hybridization or optical absorbance ($DO_{260}$) for AAV and AdV, respectively), or the viral proteins content of the vectors (RT activity and p24 content, for example for MLV and HIV, respectively). The physical particles titer measurement does not reflect the quantity of infectious and biologically-active particles which are present, because of the presence of non-infectious defective particles (defective-interfering particles or DI), without genome or with an incomplete genome.

The biological methods, in contrast, allow the determination of an infectious particles titer (ip: infectious units, plaque forming units, transduction units) (Mittereder et al., precited; Salvetti et al., Hum. Gene Ther., 1998, 9, 5, 695-706; Atkinson et al., precited) by the measurement of a biological parameter which reflects the activity of the vector in an infected cells culture:viral replication (AAV), provirus integration (retrovirus, HIV), cellular lysis [formation of plaques or foci of lysis), only in the case of lytic viruses (AdV, HSV)] and transgene expression (all types of vectors). The ip measures the number of active particles in the biological process from which the effect is measured. Thus, the vector preparations presenting a high titer of infectious particles and a low ratio of physical particles/infectious particles are considered as being of high quality, these two parameters being considered as providing quantitative information concerning the power of a preparation of a gene transfer vector.

Whatever the nature of the measured parameter, the methods described are essentially based on: serial dilutions of the vector preparation (about 10 to 20 dilutions in duplicate or triplicate), followed by vector with cells incubation time (1 to 15 days), then by cell treatment (lysis, fixation, coloration, substrate addition, hybridization, PCR), functional parameter measurement, and finally by titer determination; said titer is defined as the end-point dilution, which is the highest dilution at which the value of the biological parameter is below the detection threshold. The titer is generally determined from the curve which represents the values of the biological parameter according to the dilution of the vector:
by a linear extrapolation from the quasi-linear central region of the curve, followed by determination of the intersection with the abscissa, or
by an asymptotic estimation of said curve in the region of high dilutions; such an estimation can be made with a computer program, which is based on a hyperbolic function for the titer calculation.

Thus, the larger the number of tested dilutions, the more accurate will be the titer value.

However, these techniques have low reliability and have the disadvantage of not being standardized. To solve this problem, new methods were proposed, which are more adapted to the determination of the titer (or concentration) and the comparison of various recombinant viruses used for gene therapy (E. M. Atkinson, precited; International PCT Application WO 99/11764). For example, in the article in the name of E. M. Atkinson, precited and in the International PCT Application WO 99/11764, the method which is described comprises essentially a step of viral genetic material amplification in the host cell line, standard vector preparations of known titer obtained by serial dilutions, and an internal control of known titer. More precisely, the method includes, in several wells of a micro-titration plate, cell infection with serial dilutions of a viral preparation (10 dilutions in triplicate), replication of the viral genome in the said host cell during 48 to 72 hours, chemical lysis of said cell, hybridization of the nucleic acid, measurement of the relative quantity of viral nucleic acid replicated in each well, and the determination of the titer by linear extrapolation of the curve which represents the measured values according to the dilution of the vector.

Thus, the methods of the prior art, even the more adapted as those described by E. M. Atkinson et al., precited, do not meet practical needs for the development and the production of gene transfer vectors, for the following reasons:
their execution is difficult and comprises numerous manipulations, at each step of the method, because of the high number of samples corresponding to each vector dilution. Consequently, they cannot be used to develop and produce gene transfer vectors, which implies the treatment of numerous samples for comparing various vector constructs or various conditions for producing the vectors, or for monitoring the vector production kinetic,
they are not standardized for the most part,
they are difficult to automate, because of the number and the complexity of the steps to perform, and
the result is obtained at a fixed time which, depending on the nature of the measured parameter, varies from a few days (transgene expression) to several weeks (plaques of lysis formation). Thus, the delays required to perform these methods are not adapted to rapid determination of gene transfer vectors concentration, screening of vector libraries, control in the course of production or production kinetic monitoring of said vectors.

The present invention set itself the objective to supply a method for determining the titer of a biological agent which meets practical needs better than the methods of the prior art in that it allows the analysis of numerous samples in real time.

The invention also concerns uses of said method for the screening, the analysis and the production of gene transfer viral vectors, viral vaccines and recombinant proteins, as well as for viral infection diagnosis.

Consequently, the present invention relates to a method for determining the titer of a biological agent interacting with living target cells, characterized in that it comprises at least the following steps:

($a_1$) the incubation of said biological agent at an unknown initial concentration C, with said target cells at a constant concentration D, ($b_1$) the measurement at various successive times t, of the intensity i of the same signal, which results from the reaction biological agent+living target cells, ($c_1$) the determination of the time $t_\beta$ corresponding to the value i=β, chosen in the interval $\beta_{min}<\beta<\beta_{max}$, such that $\beta_{min}$ and $\beta_{max}$ correspond to the values of i at the inflexion point of the i=f(t) curve for respectively, the minimal and maximal concentrations of a standard biological agent, for which the $t_\beta$=f(C) curve (standard curve) is pre-established, and ($d_1$) the determination of the biological agent initial concentration C, with the help of said $t_\beta$=f(C) standard curve.

Preliminary Definitions:

biological agent means a viral or non-viral vector for gene transfer, a virus, an antibody, a vaccine or a recombinant protein.

living target cells mean target cells, in vitro or ex vivo, before their modification by a biological agent.

titer C of a biological agent means its concentration in particles (virus, gene transfer viral vector, viral vaccine) or in active molecules (recombinant proteins, antibodies), in the reaction biological agent+living target cells (C corresponds to the titer of infectious particles or ip, as defined above for gene transfer viral vectors).

reaction biological agent+living target cells means the response of the target cells to the biologic agent or to the biological process, in particular:

the expression of a reporter gene or of a transgene,
the replication, the integration or the cytolytic activity of a virus,
the enzymatic, anti-viral, oncogenic, tumor suppressor or cytotoxic activities,
the proliferation or the cellular differentiation, or
the binding to antibodies or to receptors.

The product P of the reaction biological agent+living target cells is measurable by a signal; it is determined by the measurement of a parameter which reflects the response of the living target cells to the biological agent. Without limitation, said parameter is: the protein or enzyme quantity which is expressed by a reporter gene or a transgene, the viral vector genome copy number or the cell number.

The signal means for example, the fluorescence, the luminescence, the absorbance or the cell numeration.

The signal is measured, without limitation, by using optical or fluorescence microscopy, fluorimetry, luminometry and spectrometry.

the measurement of the signal intensity means the measurement of the product P of the reaction biological agent+living target cells, without any intervention on the target cells and/or on said reaction from which product P is measured.

Standard biological agent means a biological agent identical or similar to the biological agent to analyze; said standard agent presents modifications which do not affect its activity in the reaction from which product P is measured.

measure in real time means a measure from which value is obtained instantaneously.

Surprisingly, the Inventor has shown that the signal intensity i, which reflects the response of the target cells to the biological agent, depends only on two parameters: the concentration C and the time t. Thus, when t increases, the signal intensity i increases, proportionally to the value of C; as a consequence, for a constant value of C, i varies proportionally to t and for a constant value of t, i varies proportionally to C.

In contrast to the methods of the prior art which use a constant value of t for measuring the concentration C of a biological agent, the Inventor has found unexpectedly, that the use of a constant value of C allows a simpler, more rapid and more accurate determination of the biological agents concentration.

Thus, the Inventor has showed surprisingly, that the concentration of a biological sample can be determined directly, without the need to dilute said sample, by: (1) measuring the values of i at various times t and by determining the value $t_\beta$ corresponding to the value i=β, and then (2) determining the value of C corresponding to the value $t_\beta$ on the standard curve t=f(C), such as defined above.

According to an advantageous embodiment of the method according to the invention, the standard curve is established simultaneously or before the step ($a_1$), as described above, according to the following steps:

($a_0$) the preparation of n serial dilutions of a standard biological agent, at a known initial concentration $C_0$, said dilutions corresponding to said standard biological agent final concentrations $C_1, C_2, \ldots C_n$, respectively, ($b_0$) the incubation of each standard biological agent dilution obtained in ($a_0$), with said target cells at a constant concentration D, ($c_0$) the determination of the signal intensity i which results from the reaction biological agent+target living cells, for each concentration $C_1, C_2, \ldots C_n$ of said standard biological agent, at various successive times $t_1$ to $t_n$, ($d_0$) the drawing of the i=f(t) curve for each value $C_1, C_2, \ldots C_n$, ($e_0$) the determination of the β value of i, such that $\beta_{min}<\beta<\beta_{max}$ and $\beta_{min}$ and $\beta_{max}$ correspond to the values of i at the inflexion point of the i=f(t) curve for $C_n$ and $C_1$, respectively, and ($f_0$) the drawing of the $t_\beta$=f(C) standard curve for the i=β value.

The method according to the invention is perfectly adapted to the analysis of numerous samples in real time, because it presents the following advantages:

it is simple,
it is rapid,
it is accurate,
it is standardized and
it is able to be automated.

Indeed, the method according to the invention does not require the dilution of the samples; consequently, it is particularly adapted to the analysis of numerous samples such as a gene transfer vectors library. For example, while, the methods of the prior art require the preparation of 10 to 20 dilutions to determine the titre of 30 vector samples and thus, the manipulation of 300 to 600 cell samples at each step of the method (infection, lysis, fixation, staining, substrate addition, hybridization), which implies 1800 to 2400 manipulations for a method including 3 steps (infection, lysis or fixation, and staining or substrate addition), the method according to the invention does not require sample dilution nor cell manipulation and simply implies 30 signal (i) measurements. Consequently, contrary to the methods of the prior art, the method according to the invention is simple, perfectly standardized and may be automated.

The method according to the invention is more accurate than the methods of the prior art, since the measurements are made from the same sample taken at various times t, contrary to the methods of the prior art wherein various sample dilutions are tested separately, resulting in internal variations between various dilutions.

Contrary to the techniques of the prior art which use the concentration C as a variable parameter, the method according to the invention which uses the time as a variable parameter, presents a number of advantages in that it allows the determination of biological agents concentration in real time, by measuring the signal i, by using techniques such as fluorimetry, luminometry or spectrometry.

Indeed, in the method according to the invention, the experimental values which are available immediately allow a rapid estimation of the vector concentration, in order to monitor the vector production kinetic or to analyze rapidly a gene transfer-vector library. The methods of the prior art, in contrast, do not allow such estimation since no intermediate results are available in the course of the experiment; the final result only is available, once all the data corresponding to the various dilutions have been obtained at the time t and then analyzed, which corresponds to a delay from several days to several weeks, depending on the technique used.

According to another advantageous embodiment of the method according to the invention, said signal is selected from the group consisting of the fluorescence, the luminescence, the absorbance and the cell numeration.

Without limitation, the signal is advantageously measured by a technique such as: optical or fluorescent microscopy, fluorimetry, luminometry and spectrometry.

According to yet another advantageous embodiment of the method according to the invention, said biological agent is selected from the group consisting of viruses, viral and non-viral vectors for gene transfer, vaccines, antibodies and recombinant proteins.

The present invention relates also to a kit for quantifying (titration) or detecting a biological agent, characterized in that it comprises:
  living target cells at a constant concentration D,
  a standard biological agent at known concentration C, and the $t_\beta = f(C)$.standard curve of said standard biological agent.

This kit is associated with an appropriate physical mean to measure the signal intensity of the reaction biological agent+living target cells.

This kit which allows real time measurements is particularly adapted to the titer determination (titration) of a vector for use in gene therapy, a virus for use as a vaccine, a recombinant protein for use as a biological product (medicament, reagent), or to the quantification and/or to the detection of a virus, for viral infection diagnosis.

Apart from the foregoing provision, the invention also comprises other provisions which will become apparent from the following description referring to examples of how to carry out the method forming the subject of the present invention and to the attached drawings, in which.

It must be clearly understood, however, that these examples are given solely in order to illustrate the subject of the invention without in any way implying limitation.

EXAMPLE 1

Determination of the Titer of a Retroviral Vector in Rat-2 Cells 1.1—Materials and Methods The biological agent is a retroviral vector called pSI-EGFP (Ropp et al., Cytometry, 1995, 21, 309-317), coding for the fluorescent eukaryotic protein (Eukaryotic Green Fluorescent Protein or EGFP) reporter gene, the target cells are Rat-2 cells (ATC CRL1764) and the reaction biological agent+living target cells is the expression of the EGFP reporter gene. The product P which is measured for determining the titer of said vector (concentration in retroviral infectious particles or ip) is the quantity of EGFP protein, which is measured by fluorimetry.

Rat-2 cells are seeded in wells of a micro-titration plate at a constant concentration, then infected at t=0, with the ½, ¼ and 1/10 dilutions of a standard retroviral vector preparation of known initial concentration ($C_0 = 10^6$ infectious particles/ml), said dilutions corresponding to the concentrations of $0.5 \times 10^6$; $0.25 \times 10^6$ and $0.1 \times 10^6$ infectious particles/ml, respectively. At times t=16 hours, 24 hours, 40 hours, 48 hours and 64 hours, the fluorescence intensity signal i, emitted by cells infected with each vector dilution is measured by fluorimetry. The curve i=f(t) is then drawn for each dilution and the value of $\beta$ is fixed at 100. The values $t_\beta$, corresponding to the values of t when i=100, are determined for each concentration of the standard samples, then, the curve $t_\beta = f(C)$ is drawn from these values.

1.2—Results

Figure 1:
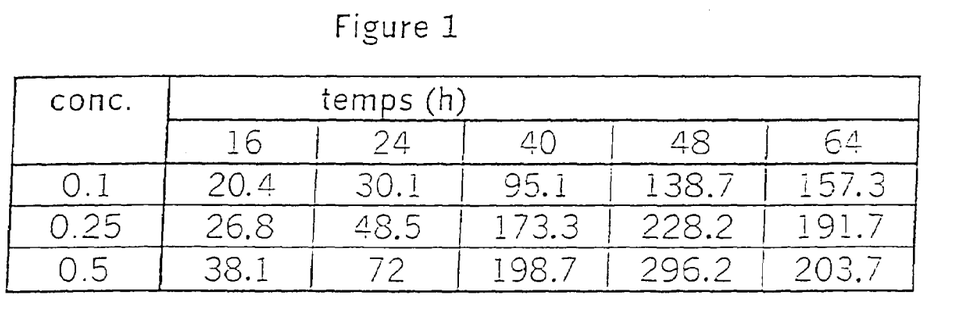
FIG. 1 represents the experimental values of the fluorescence signal intensity i, according to the time t, for each concentration (conc.) of a retroviral vector coding for the EGFP fluorescent protein. The concentrations are expressed for $10^6$ infectious particles/ml.
Figure 2:
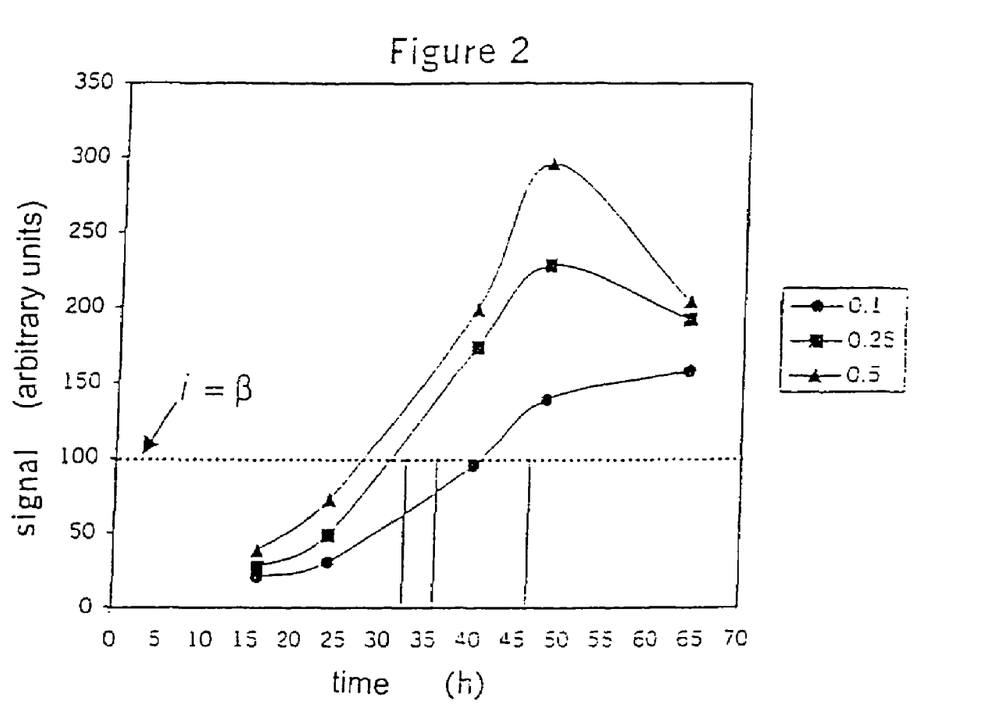
FIG. 2 represents the i=f(t) curve, determined from the experimental values presented in FIG. 1.
Figure 3:
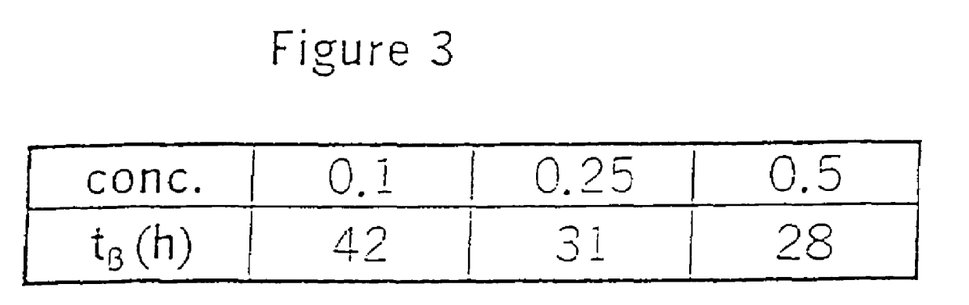
FIG. 3 represents the values $t_\beta$ for various vector concentrations, determined from the curve in FIG. 2, for the $\beta=100$ value of i.
Figure 4:
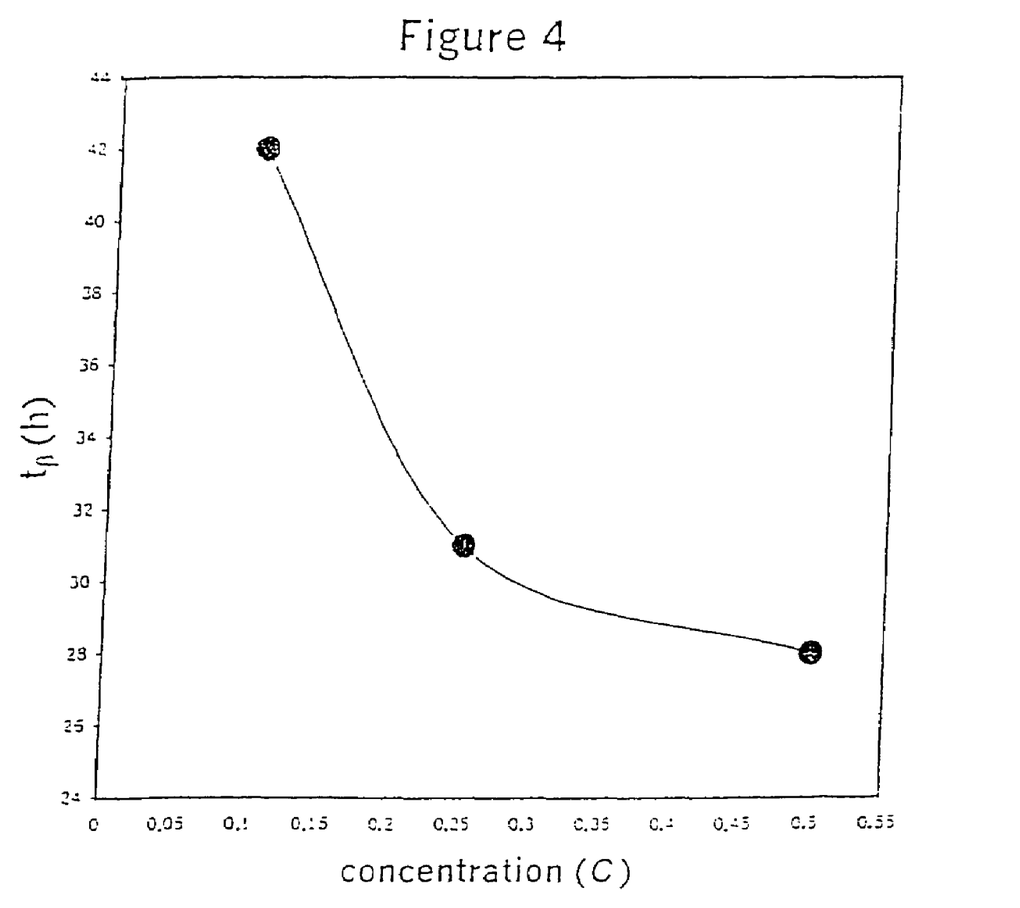
FIG. 4 represents the $t_\beta = f(C)$ standard curve of the retroviral vector, determined from the experimental values presented in FIG. 3.

FIG. 2 represents the i=f(t) curve, determined from the experimental values presented in FIG. 1. FIG. 4 represents the $t_\beta$=f(C) standard curve of the retroviral vector, determined from the experimental values presented in FIG. 3.

FIG. 2 shows that the signal intensity is a function of the vector incubation time with the target cells t, and the vector concentration C.

FIG. 2 shows also that the $\beta$=100 value, allows a sensitive and accurate determination of the vector concentration since (i) it detects low concentrations of the vector, and (ii) for this value, the variations of C correspond to an important variation of t. These results are confirmed by FIG. 4 which represents the $t_\beta$=f(C) standard curve of the vector. This standard curve shows that there is a direct relationship between the values of $t_\beta$ and C which allows the determination of the vector preparation concentration, without dilution and without manipulation of cells, simply by determination of the $t_\beta$ experimental value of this vector, corresponding to the $\beta$=100 value.

EXAMPLE 2

Comparison of the Titer of a Recombinant Adeno-Associated Virus (rAAV) Determined from the Parameters of a Classical Method (Constant Time and Variable Concentration) or of the Method According to the Invention (Variable Time and Constant Concentration)

2.1—Materials and Methods

The biological agent is a recombinant adeno-associated virus (rAAV), coding for the reporter gene lacZ, the target cells are Hela-repcap32 cell line, the reaction biological agent+living target cells is the viral replication and the product P which is measured for determining the titer of the vector (concentration in active particles or ip) is the rAAV genome copy number. P is measured by Dot-blot hybridization, according to standard techniques known by a skilled person in the art.

Hela-repcap32 cells are seeded in wells of a microtitration plate at constant concentration, then co-infected at t=0, at a multiplicity of infection of 100, with $10^{-4}$, $10^{-7}$, $10^{-8}$ and $10^{-9}$ vector dilutions and the wild-type adenovirus.

Cells are harvested at various times t=6 hours, 14 hours, 18 hours, 20 hours, 24 hours, 30 hours, 38 hours, 44 hours, 48 hours and 54 hours, then the viral genome is isolated and hybridized with a nucleotidic labelled probe, according to the classic Dot-Blot method, known by a skilled person in the art. The signal intensity, which represents the hybridized DNA quantity, is measured by means of a phosphoimager.

For the determination of the titer according to the classical method, the log i=f(log dilution) curve is drawn from the values obtained at the time t=24 hours and the titer is determined by asymptotic estimation in the region of the highest dilutions.

For the determination of the titer according to the method of the invention, the log i=f(t) curve is drawn for each vector dilution and the $\beta$ value is fixed to −2. The $t_\beta$ values, corresponding to the values of t when i=−2, are determined for each concentration of the standard agent, then, the $t_\beta$=f(log C) curve is drawn from these values.

2.2—Results

Figure 5:
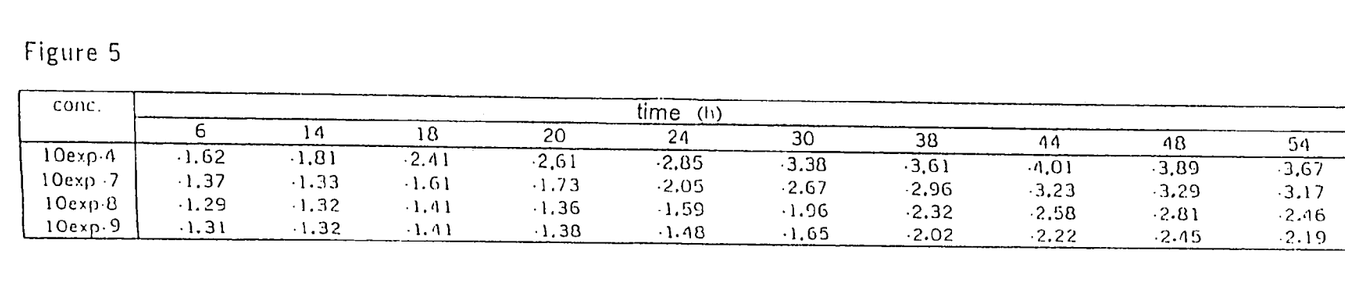
FIG. 5 represents the experimental values of the hybridization signal intensity i, according to the time t, for each dilution of an adenovirus associated recombinant vector (rAAV).
Figure 6:
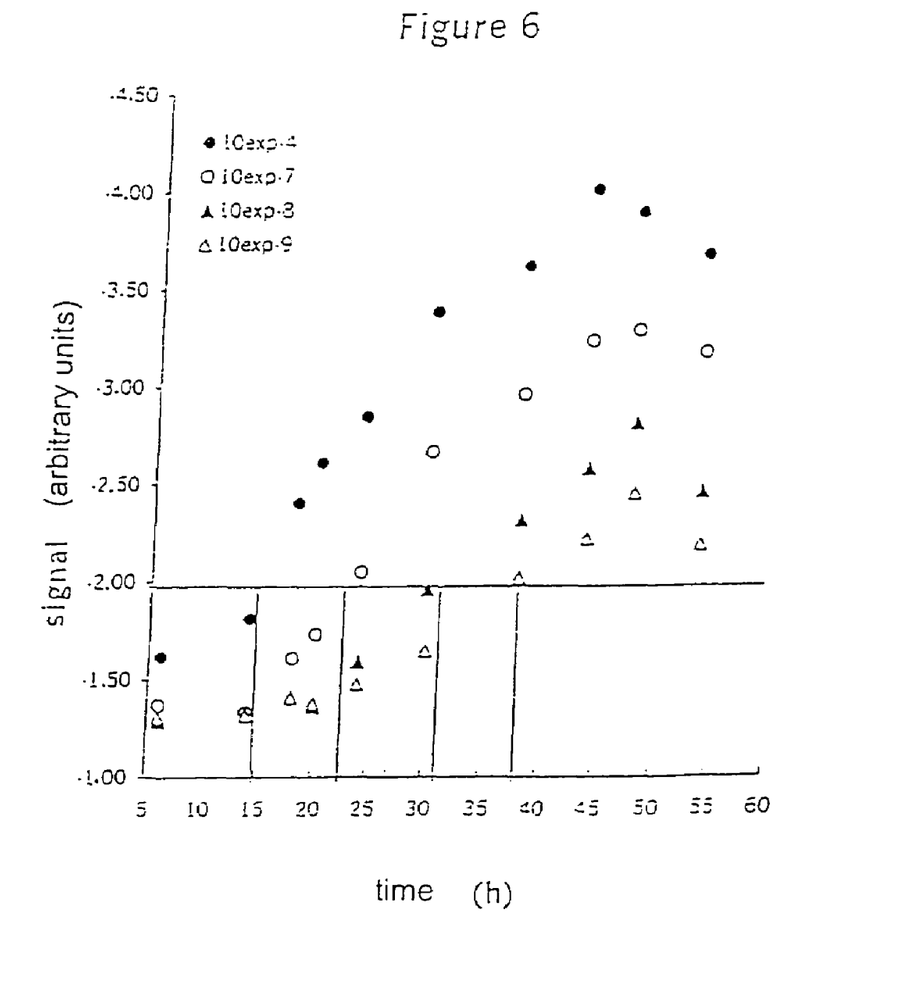
FIG. 6 represents the i=f(t) curve, determined from the experimental values presented in FIG. 5.
Figure 7:
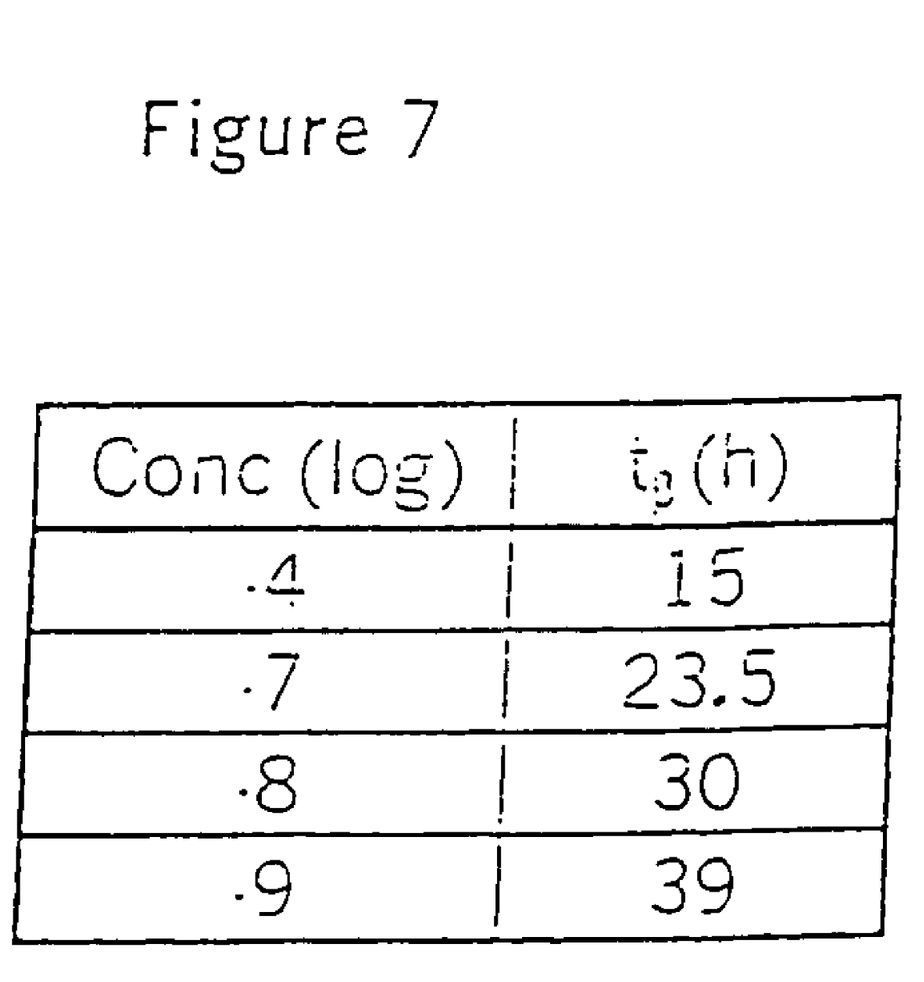
FIG. 7 represents the values of $t_\beta$ for various concentrations of vector, determined from the curve presented in FIG. 6, for the value $\beta=2$ of i.
Figure 8:
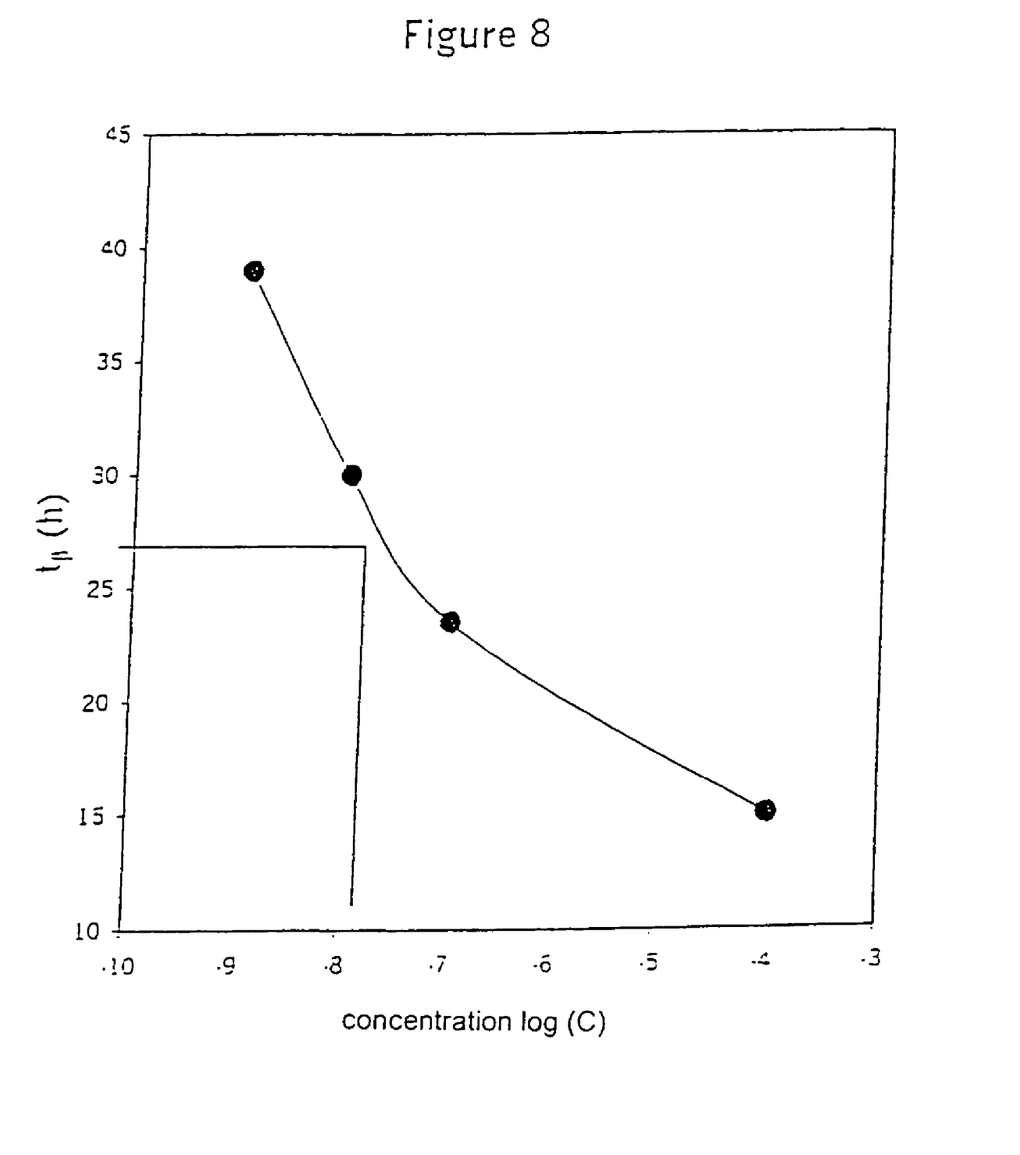
FIG. 8 represents the $t_\beta = f(C)$ standard curve of the vector rAAV, determined from the experimental values presented in FIG. 7.

FIG. 6 represents the log i=f(t) curve, determined from the experimental values presented in FIG. 5. FIG. 8 represents the $t_\beta$=f(log C) standard curve of the vector rAAV, determined from the experimental values presented in FIG. 7.

FIG. 6 shows that the signal intensity is a function of the vector incubation time with cells t and the vector concentration C. FIG. 6 shows also that the $\beta$=−2 value allows a sensitive and accurate determination of the vector concentration, since (i) it detects low vector concentrations, and (ii) for this value, the variations of C correspond to an important variation of t.

These results are confirmed by FIG. 8 which represents the $t_\beta$=f(log C) standard curve of the vector. This standard curve shows that there is a direct relationship between the $t_\beta$ and C values which allows the determination of a vector preparation concentration, accurately and without dilution, from a single experimental value of $t_\beta$ corresponding to the $\beta$=−2 value.

By comparison, for the same vector preparation, the classical method gives a titer of $1 \times 10^8$ infectious particles/ml and the method according to the invention gives a titer of $0.85 \times 10^8$ infectious particles/ml. These results show that the values obtained by the method according to the invention are comparable to those obtained by the classical methods for titration of biological agents.

Nevertheless, contrary to the classical methods, the method for determining the titer of biological agents according to the invention allows advantageously the analysis of numerous samples, simultaneously and in real time. Indeed, it is simple, rapid, accurate, standardized, it can be automated and the value of the signal intensity which measures the product of the reaction of the biological agent with the living target cells is obtained immediately, without intervention on the target cells and on the biological reaction from which product is measured.

So, the method according to the the invention is useful for:
- the rapid screening of gene transfer vectors or recombinant protein mutants libraries,
- the production optimization or control of: therapeutic gene-transfer vectors for use in pre-clinical studies and phase I clinical trials, viruses for use as viral vaccines, or recombinant proteins for use as medicaments or biological reagents, and
- rapid detection of a viral infection from a patient biological sample.

As is apparent from the foregoing description, the invention is in no way limited to those modes of execution, embodiments and modes of application which have now been described more explicitly; on the contrary, it encompasses all the variants therof which may occur to those skilled in the art, without deviating from the framework or the scope of the present invention.

The invention claimed is:

1. A method for determining the titer (concentration of virus or viral or non-viral vector particles) of a virus or viral or non-viral vector which interacts with living target cells and produces a product P, comprising:

($a_1$) incubating a virus or a viral or non-viral vector at an unknown initial concentration C with living target cells at constant initial concentration D, for a time and under conditions suitable for interaction of said virus or viral or non-viral vector with the living cells, and for the production of product P, wherein measurement of a parameter of product P which reflects the response of the living target cells to the virus or viral or non-viral vector particles provides a measurable signal, ($b_1$) measuring at various successive times t the intensity i of the signal produced by the interaction of said virus or viral or non-viral vector and said target cells, ($c_1$) determining $\beta$, the value of i at the inflexion point of the i=f(t) curve for the virus or viral or non-viral vector, ($c_2$) determining the time $t_\beta$ corresponding to the i=$\beta$ value, chosen in the interval $\beta_{min}<\beta<\beta_{max}$, wherein $\beta_{min}$ and $\beta_{max}$, respectively correspond to the values of i at the inflexion point of the i=f(t) curve for the minimal and maximal concentrations of a standard virus or viral or non-viral vector, for which the $t_\beta$=f(C) curve is pre established, and ($d_1$) determining the initial concentration C of the virus or viral or non-viral vector using a $t_\beta$=f(C) standard curve.

2. The method of claim 1, wherein, simultaneously or before the step ($a_1$), the standard curve is established according to the following steps:

($a_0$) preparing n serial dilutions of a standard virus or viral or non-viral vector at a known initial concentration $C_0$, corresponding to said virus or viral or non-viral vector final concentrations $C_1, C_2, \ldots C_n$, respectively, ($b_0$) incubating each standard virus or viral or non-viral vector dilution obtained in ($a_0$), with said target cells at a constant initial concentration D, ($c_0$) determining the intensity i of the signal produced by the interaction of the virus or viral or non-viral vector and the living target cells for each standard virus or viral or non-viral vector concentration $C_1, C_2, \ldots C_n'$ at successive times $t_1$ to $t_n'$ ($d_0$) drawing the i=f(t) curve for each value of $C_1, C_2, \ldots C_n'$ ($e_0$) determining the $\beta$ value of i, chosen in the interval $\beta_{min}<\beta<\beta_{max}$ wherein $\beta_{min}$ and $\beta_{max}$ respectively correspond to the values of i at the inflexion point of the i=f(t) curve for $C_n$, and $C_1$, and ($f_0$) drawing the $t_\beta$=f(C) standard curve for the i=$\beta$ value.

3. The method of claim 1, wherein the virus or viral or non-viral vector is a virus.

4. The method of claim 1, wherein the virus or viral or non-viral vector is a virus gene transfer vector.

5. The method of claim 1, wherein the virus or viral or non-viral vector is a non-viral gene transfer vector.

6. The method of claim 1, wherein the biological agent is a viral vaccine.

7. The method of claim 1, wherein the measurable signal is obtained by measuring a parameter of the virus or viral vector genome copy number in said target cells.

* * * * *